(12) United States Patent
Bridges

(10) Patent No.: US 8,158,119 B2
(45) Date of Patent: Apr. 17, 2012

(54) CARDIAC TARGETED DELIVERY OF CELLS

(75) Inventor: Charles R. Bridges, Villanova, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 696 days.

(21) Appl. No.: 12/086,024

(22) PCT Filed: Dec. 4, 2006

(86) PCT No.: PCT/US2006/046292
§ 371 (c)(1), (2), (4) Date: Jun. 4, 2008

(87) PCT Pub. No.: WO2007/067502
PCT Pub. Date: Jun. 14, 2007

(65) Prior Publication Data
US 2009/0287185 A1 Nov. 19, 2009

Related U.S. Application Data

(60) Provisional application No. 60/742,244, filed on Dec. 5, 2005.

(51) Int. Cl.
*A01N 63/00* (2006.01)
*A01N 65/00* (2009.01)

(52) U.S. Cl. ...................................... 424/93.1; 424/93.7

(58) Field of Classification Search ........................ None
See application file for complete search history.

(56) References Cited

U.S. PATENT DOCUMENTS

| 5,451,207 A | 9/1995 | Yock |
|---|---|---|
| 5,813,842 A | 9/1998 | Tamari |
| 6,071,258 A | 6/2000 | Dalke et al. |
| 6,267,747 B1 | 7/2001 | Samson et al. |
| 6,508,777 B1 | 1/2003 | Macoviak et al. |
| 6,699,231 B1 | 3/2004 | Sterman et al. |
| 6,726,651 B1 | 4/2004 | Robinson et al. |
| 7,214,369 B2 | 5/2007 | Wolff |
| 7,722,596 B2 | 5/2010 | Shapland et al. |
| 2003/0040665 A1 | 2/2003 | Khuri |
| 2004/0126879 A1 | 7/2004 | Schneider et al. |
| 2006/0258980 A1 | 11/2006 | Bridges |
| 2007/0073264 A1 | 3/2007 | Stedman |

FOREIGN PATENT DOCUMENTS

| WO | WO 99/31982 A1 | 7/1999 |
|---|---|---|
| WO | WO 2005/027995 A2 | 3/2005 |
| WO | WO 2005/030292 A2 | 4/2005 |
| WO | WO 2006/039218 A2 | 4/2006 |

OTHER PUBLICATIONS

Bridges et al, Global Cardiac-Specific Transgene Expression Using Cardiopulmonary Bypass with Cardiac Isolation, Annals of Thoracic Surgery, 73:1939-1946, (Jun. 2002).
Dotsenko, et al., Endogenous stem cells in patients undergoing coronary artery bypass graft surgery, European Journal of Cardio-thoracic Surgery, May 24, 2009, pp. 563-571, vol. 36.
Giordano, et al., Retrograde Coronary Perfusion: A Superior Route to Deliver Therapeutics to the Heart?, Journal of the American College of Cardiology, Sep. 17, 2003, vol. 42, No. 6.
Vulliet, et al., Intra-coronary arterial injection of mesenchymal stromal cells and microinfarction in dogs, Lancet, Mar. 6, 2004, Abstract Only (full article at pp. 783-784, vol. 363, No. 9411).
Wang, et al., Stem Cells for Myocardial Repair With Use of a Transarterial Catheter, Circulation, 2009 (presented in part Nov. 8-12, 2008), pp. S238-S246, vol. 120, suppl. 1.
Aug. 16, 2010 Office Action in co-owned U.S. Appl. No. 11/664,245.
Jan. 17, 2011 Response to Aug. 16, 2010 Office Action in co-owned counterpart U.S. Appl. No. 11/664,245.
Feb. 24, 2011 Office Action in co-owned U.S. Appl. No. 11/664,245.
Jun. 24, 2011 Response to Feb. 24, 2011 OA in co-owned U.S. Appl. No. 11/664,245.
Aug. 11, 2011 Office Action in co-owned U.S. Appl. No. 11/664,245.

*Primary Examiner* — Anne-Marie Falk
(74) *Attorney, Agent, or Firm* — Howson & Howson LLP

(57) ABSTRACT

A method of delivering cardiac stem cell and treating damaged cardiac tissue is provided. The method involves isolation of subject's cardiac circulation from the subject's systemic circulation and perfusing a solution comprising stem cells into the cardiac circuit.

10 Claims, 4 Drawing Sheets

CARDIAC TARGETED DELIVERY OF CELLS

CROSS-REFERENCE TO RELATED APPLICATIONS

This is a national stage application under 35 U.S.C. 371 of PCT/US2006/046292, filed on Dec. 4, 2006, which claims the benefit under 35 USC 119(e) of U.S. patent application Ser. No. 60/742,244, filed Dec. 5, 2005.

STATEMENT REGARDING FEDERALLY SPONSORED RESEARCH OR DEVELOPMENT

This application contains work supported by grants from the National Institutes of Health (NIH), NIBIB 1-R21-EB003223-01 and NIBIB 5-R21-EB003223-02. The US government may have certain rights in this invention.

BACKGROUND OF THE INVENTION

The present invention relates to treatment of damaged cardiac tissue.

Cardiovascular disease is a leading cause of death in the United States, and heart failure is a major public health problem in the United States. Gene therapy may provide promising new therapies for this vexing public health problem. However, gene delivery is the most important as yet unsolved problem limiting the applicability of gene therapy for the treatment of heart failure. This applies equally to heart failure due to defined X-linked or autosomal recessive gene defects and to the more common forms of heart failure without a well-defined genetic basis since promising vectors and therapeutic transgenes have been identified for both.

Bridges et al., Annals of Thoracic Surgery, 73: 1939-1946 (2002) describe a cardiopulmonary surgical technique for a so-called "incomplete isolation" of a subject's heart in situ. The cardiac isolation technique requires the formation of two separate cardiopulmonary bypass circuits, one for systemic circulation of the body and one for antegrade cardiac circulation of a gene delivery vector. The technique enables multiple passes, or recirculation, of a macromolecular complex through a subject's heart during cardiopulmonary bypass surgery.

A technique which isolates the heart to permit systemic delivery of genes is described in International Publication No. WO 2005/030292 (Apr. 7, 2005), and its corresponding U.S. national phase application Ser. No. 10/573,129. In addition, a balloon catheter useful in retrograde perfusion of the heart with drugs, gene therapy vectors or other solutions via the coronary sinus is described in U.S. patent application Ser. No. 10/572,238 and its corresponding International Publication No. WO 2005/027995, published Mar. 31, 2005.

A cardiac isolation circuit has been described for use in delivery of macromolecular complexes. See, e.g., International Patent Application No. PCT/US2005/34283, published as WO 2006/039218.

There is need for new methods for treating cardiac injury and disease.

SUMMARY OF THE INVENTION

Advantageously, the present invention provides a method of delivering cells to the heart. In one embodiment, the invention permits for efficient delivery of cellular materials during complete cardiac isolation. The method allows for delivery of stem cells, and particularly, cardiac stem cells, for the repair and treatment of damaged cardiac tissue.

Other aspects and advantages of the invention will be apparent from the following detailed description of the invention.

DETAILED DESCRIPTION OF THE INVENTION

Figure 1:
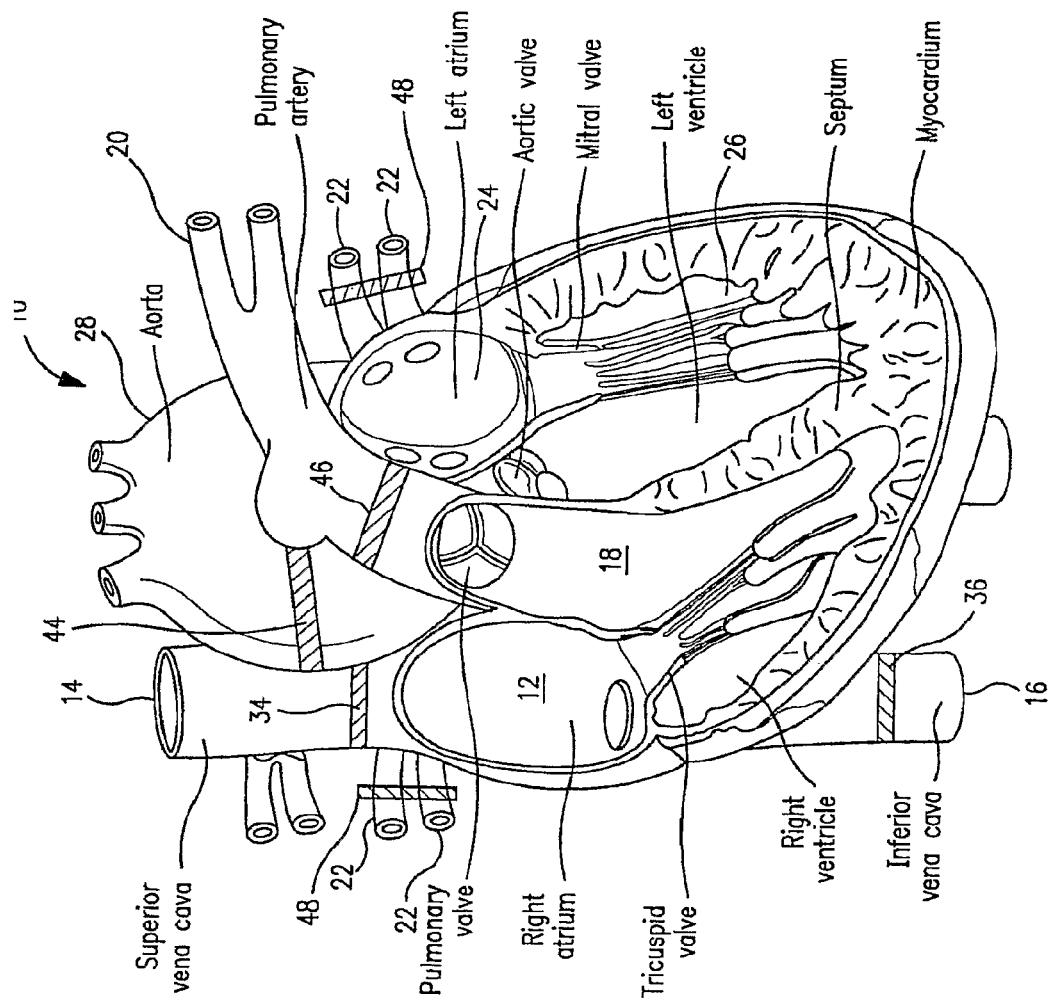
FIG. 1 is a view of a heart.

The present invention provides a novel method for treatment of damaged and/or diseased cardiac tissue by targeted delivery of pluripotent stem cells to the heart.

In one embodiment, the method of the invention requires a lower number of cells for infusion would be required using a systemic circuit. Similarly, the invention requires a lower number of cells for infusion would be required using simple intracoronary injection or intravenous injection. Additionally, the fact that the method of the invention can be performed in isolation reduces the risk of stem cells, particularly those from non-cardiac tissues from non-cardiac sources differentiating into other cell types since these cells will be largely confined to the heart by the invention and will not gain access to other organs where differentiation into undesirable cell types might more likely occur. Furthermore, neoplastic disease (benign and malignant tumors, leukemia, and lymphoma) would be least common since these cells will be cleared from the blood stream (of both heart and body) after administration to the heart thus limiting the potential for harmful effects on other organs and tissues.

The need for a decreased number of cells is provided by the decrease in circuit volume provided by the isolated cardiac circuit used in the method of the invention and the fact that there is no dilution of the cells that would occur if the cells were infused systemically. Further, in one embodiment, the dwell time in the heart permitted by the circuit used in the invention also contributes to the need for a decreased number of cells. Because fewer cells are required by the method of the invention, less culture time is required and cells may be delivered sooner following infarction or other cardiac damage. Thus a therapeutic effect can be achieved earlier before irreversible damage has occurred.

Desirably, the cells used in method of the invention include pluripotent stem cells which differentiate into cardiac myocytes and/or other cells which can mimic the function of cells in cardiac tissue such as endothelial cells and smooth muscle cells necessary for blood vessel formation in the heart. In one embodiment, bone marrow cells containing hematopoietic stem cells are used in the method of the invention. In another embodiment, cardiac stem cells are used in the method of the invention. Use if genetically modified cells may constitute a means of delivering proteins or genes to the heart. However, other cells may be used in the method of the invention.

In one embodiment, the method of the invention is useful as an adjunct to valve repair or replacement surgery, coronary artery bypass graft surgery or ventricular assist device (VAD) implantation procedures in selected patients, e.g., patients with heart failure. The method of the invention are also useful in patients with known X-linked or autosomal recessive cardiomyopathy. Another embodiment of the method includes the use of a modified circuit without the need for the use of cardiopulmonary bypass where a portion of the effluent is returned to the heart or recirculated through the heart even if incomplete isolation of the heart is achieved. A variety of other applications for the method of the invention will be readily apparent to one of skill in the art.

Transferring Stem Cells to the Heart of a Subject.

In one embodiment, the cells delivered to a subject according to a method of the invention are from a heterologous source. The term "heterologous" includes, among other things, cells from a source other than the subject. Such cells may be from a human donor or from a non-human mammalian source, e.g., pigs or primates. As used herein "heterologous" may also include molecules that are not natively found in combination with the material with which they are being associated. For example, a heterologous molecule is not found in a target cell in the form in which it is delivered to the cell. As another example, heterologous refers to molecules, including nucleic acid sequences, which are derived from the same source but are natively non-contiguous, or molecules that are derived from different sources.

In another embodiment, autologous cells are obtained from the subject. Such cells may have been previously obtained from the subject and stored for future use, or obtained from a sample taken closer to the time of infusion (e.g., within days, weeks or months thereof). These cells may be expanded in culture to increase their numbers prior to use.

Desirably, the cells delivered according to the present invention include stem cells, e.g., hematopoietic and non-hematopoietic stem cells from bone marrow and small stem cell populations which reside in the heart or in skeletal muscle. For example, cardiac stem cells can be isolated from tissue obtained from a biopsy from cardiac tissue, e.g., the right ventricle or right atrium. The sample is collected using techniques well known to those of skill in the art. In another example, stem cells are obtained from a sample of bone marrow cells. The cells are then cultured in suitable media and delivered via the method of the invention. Suitable media for proliferating stem cells has been described. See, e.g., U.S. Published Patent Application No. U.S. 2005 233446 and International Published Patent Application No. WO 2005 090557. Still other types of media are known to those of skill in the art.

For use in the present invention, the selected cells are infused in a physiologically compatible solution. In one embodiment, the solution contains physiologic solution that may be readily selected from among saline, isotonic dextrose, or a glycerol solution, among others that will be apparent to one of skill in the art given the information provided herein. The physiologic solution may be oxygenated; however, the invention is not so limited.

The concentration of the cells in the solution can vary depending upon the indication. For example, a suitable concentration may be in the range of about $1 \times 10^4$ to $1 \times 10^7$, or about $10^6$ cells per 1 mL physiologic solution. Further, a solution may contain one or more other active agents, e.g., a permeabilizing agent, a macromolecular complex, enzyme, or other moiety, or two or more proteins, enzymes, or other moieties. However, given the information provided in the present invention, one of skill in the art can readily select higher or lower volumes.

Thus, the present invention provides a method for delivery of the cells to the heart tissue. As described, the use of retrograde perfusion and a small circuit without dilution from the systemic circulatory system permits high levels of transfer into the venous interstitium, thereby enhancing transfer into the cardiac muscle as compared to methods known in the art and avoiding transfer of the cells to the remainder of the subject.

In order to perfuse the heart of a subject according to the present invention, the following general procedure is followed. Typically, the subject is cannulated (e.g., in the left femoral artery) for blood pressure monitoring. The aorta and pulmonary artery are ensnared using umbilical tapes. The pulmonary artery is ensnared by exclusion. The right carotid artery is cannulated. Using previously placed purse strings: 1) a cardioplegia cannula (containing a vent limb) is placed in the ascending aorta; 2) the superior vena cava is cannulated; 3) a retrograde catheter is placed into the coronary sinus and 4) the inferior vena cava is cannulated. The two venous cannulae are connected to a Y connector and connected to the venous limb of the pump circuit. Cardiopulmonary bypass (CPB) is initiated. All of the pulmonary veins are ensnared, individually or in groups using umbilical tapes and tourniquets. The azygous vein is ligated. The IVC is snared; a cannula is placed into the left ventricular cavity and clamped. A cannula is then placed into the right ventricle and clamped and the purse string is snared. Although the method described above is typically used, the invention also incorporates minimally invasive modifications where the pulmonary artery, aorta, superior and inferior vena cava and pulmonary veins are temporarily occluded using balloon catheters to achieve the same functional isolation of the heart.

Figure 2:
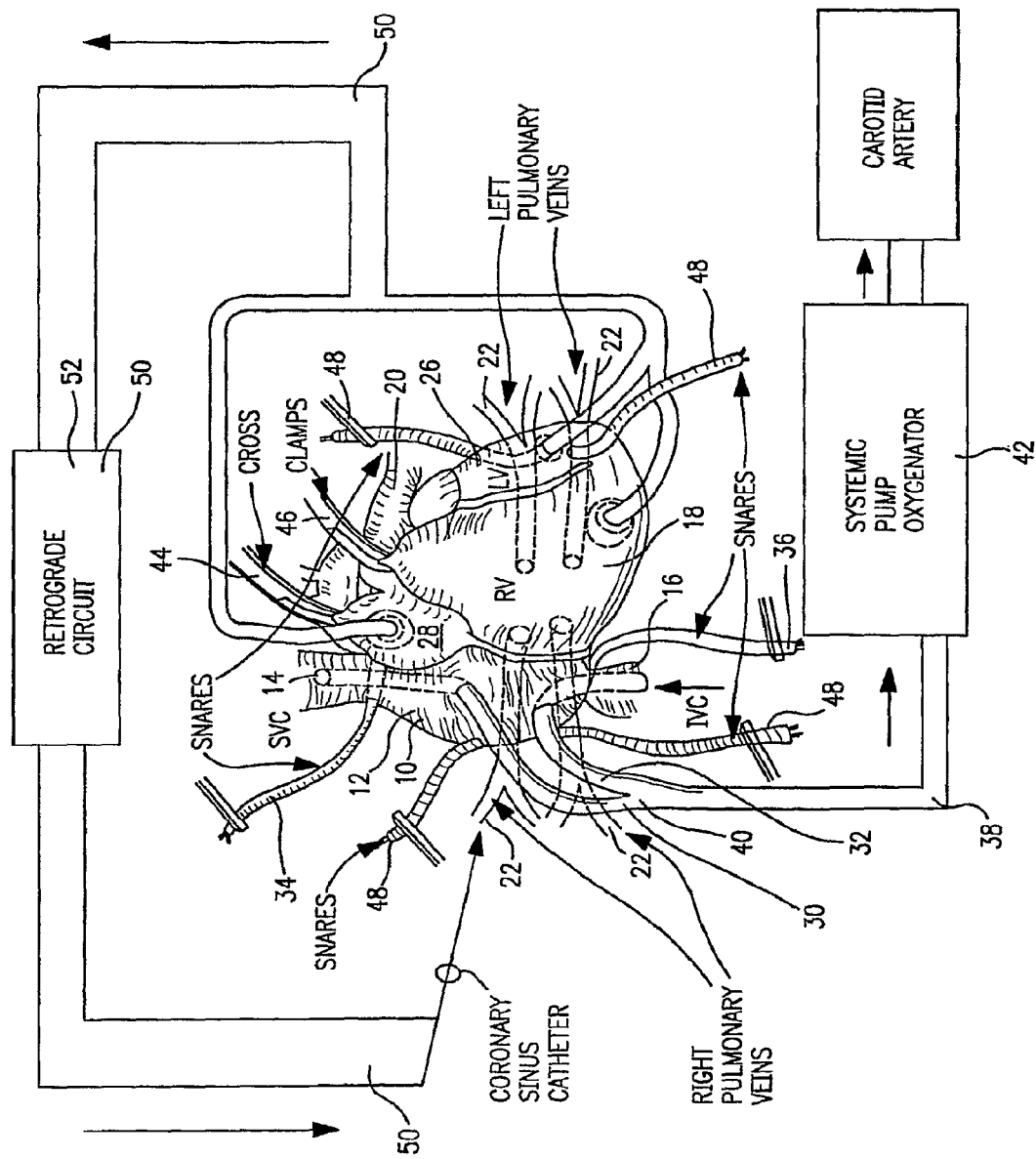
FIG. 2 is a view of a perfusion circuit useful in the present invention.

The cardiac circuit, illustrated schematically in FIG. 2, is constructed as described in detail herein. Systemic cooling to, in the range of 15 to 32° C., and preferably, about 30° C. is initiated. The coronary circuit is isolated and the heart emptied of excess volume and air.

Flow into the now isolated cardiac circuit is resumed until the coronary sinus pressure equals between about 50 mm Hg to 100 mm Hg, and preferably, about 60 to 80 mm Hg (typically flow is approximately 100-150 mL/min).

Then a solution containing cells (usually about 0.5 to 3 mL/kg, and preferably about 2.5 mL/kg) is injected slowly into a suitable volume. Suitably, the total volume of the solution infused into the heart is in the range of 20 to 100%, 25 to 90%, 30 to 80%, 40 to 70%, 50 to 60%, of the estimated volume of the heart. For slow injection, infusion is generally over 30 seconds to 1 minute at a circuit flow rate of about 80 cc/min to 140 cc/min, preferably about 100 to 120 cc/min.

In one embodiment, the circulation is stopped and the solution is allowed to dwell for about 30 seconds to ten minutes, or about 1 minute to 9 minutes, or about 2 to 5 minutes. Flow is then restored over one minute to 100 to 120 cc/min, with coronary sinus pressure equal to 60 to 80 mm Hg and the an additional volume of solution is slowly infused and the solution recirculated. During this interval, the flow is slowly increased to a maximum of 150 cc/min as needed to maintain a coronary sinus pressure of 60 to 80 mm Hg. Suitably, recirculation is for up to 20 minutes where the circulation has been stopped for 10 minutes. Recirculation may be longer where there has been a shorter dwell time. According to the invention, the same solution or a different solution (e.g., containing different cells or a macromolecular complex) can be infused to the heart upon restarting the circulation.

In another embodiment, there is no dwell time, i.e., the circulation is not stopped. In such a circumstance, the solution can be allowed to recirculate for as long as 30 minutes. However, shorter times, e.g., 20 minutes, may be desirable.

The coronary sinus catheter is then removed and the suture tied. The coronary circuit is then flushed, conventional techniques for removing the subject from cardio-pulmonary bypass are utilized [see, Bridges, et al, cited above] and rewarming is initiated. Where the infusion has been retrograde, the coronary circuit is generally flushed in an antegrade fashion.

Typically, this involves infusion of a suitable solution via the aortic route (e.g, the ascending aorta).

In still another aspect, the method of the invention delivers a solution containing, at least cells, simultaneously in both the retrograde and antegrade direction during complete cardiac isolation.

Suitably, the circuit described herein, optionally utilizing the dual balloon catheter system, can be modified so that rather than infusing solely in a retrograde manner, i.e., into the coronary sinus, infusion is both through the coronary sinus and the aortic route (i.e., antegrade). Outflow is still through the left and right ventricles. In this embodiment, the benefits of elevated venous pressure with more global myocardial delivery are combined.

In an alternative embodiment, the method described above is followed, with the exception that the retrograde catheters described in WO 2005/027995, published Mar. 31, 2005, which allow for global retrograde delivery, are utilized. These catheters are expected to overcome the limitations observed in the prior art catheters utilized in the study described herein, which deliver less solution to the right ventricle than was desired.

In yet another embodiment, the method of the invention is performed with simultaneous (antegrade/retrograde) cardioplegia delivery in which substantially higher retrograde pressures (up to 80 mm Hg or higher) may be achieved without apparent myocardial injury.

In yet another embodiment, the method of the invention incorporates minimally invasive modifications where the pulmonary artery, aorta, superior and inferior vena cava and pulmonary veins are temporarily occluded using balloon catheters to achieve the same functional isolation of the heart.

In another embodiment, incomplete isolation of the heart is achieved either using conventional or minimally invasive (catheter-based) surgical approaches but dwell and or recirculation of the solution through the heart still results in a reduction in the total number of cells required to achieve the same level of engraftment in the heart.

In another embodiment the heart is only partially isolated or intermittently isolated for brief periods and cardiopulmonary bypass is not utilized.

The method of the invention is useful for treatment of injury to the cardiac muscle caused by myocardial infarction or a variety of other conditions including, e.g., inherited autosomal recessive conditions, such as those associated with the sarcoglycan deficiencies, X-linked cardiomyopathy or the cardiomyopathy associated with Becker's muscular dystrophy. Other types of therapies include, e.g., treatment of genetic cardiomyopathies or "idiopathic" heart failure. In addition, the methods of the invention can be used as an adjunct to valve repair or replacement surgery, coronary artery bypass graft surgery or ventricular assist device (VAD) implantation procedures in selected patients with heart failure or post myocardial injury.

The cells described herein may be delivered alone, or optionally, in combination with a macromolecular complex as defined herein. Still other therapies include the simultaneous or metachronous delivery of cells in combination with the delivery of angiogenic compounds to the heart (and particularly, the myocardium) to treat coronary ischemia. In another example, compounds useful for cancer therapies, including, e.g., chemotherapeutic agents useful in treatment of cardiac sarcomas and other neoplasms, can be used.

As used herein, the term "macromolecular complex" encompasses any biologically useful moiety that can be transferred into the targeted cells (e.g., striated cardiac muscle cells, or other muscle cells or tissues). Examples of suitable macromolecular complexes include vectors composed of nucleic acids, including RNA and DNA molecules, dominant negative mutants, enzymes, proteins, peptides, or non-proteinaceous molecules, which may include small molecules or other chemical moieties.

Examples of suitable chemical agents and/or small molecules include, e.g., alkylating agents (i.e., cisplatin, carboplatin, streptazoin, melphalan, chlorambucil, carmustine, methclorethamine, lomustine, bisulfan, thiotepa, ifofamide, or cyclophosphamide); hormonal agents (e.g., estramustine, tamoxifen, toremifene, anastrozole, or letrazole; antibiotics (e.g., plicamycin, bleomycin, mitoxantrone, idarubicin, dactinomycin, mitomycin, or daunorubicin); immunomodulators (e.g., interferons, IL-2, or BCG); antimitotic agents (e.g., vinblastine, vincristine, teniposide, or vinorelbine); tipoisomerase inhibitors (e.g., topotecan, irinotecan, etoposide, or doxorubicin); and other agents (e.g., hydroxyurea, traztuzumab, altretamine, retuximab, paclitaxel, docetaxel, L-asparaginase, or gemtuzumab, ozogamicin).

Still other suitable macromolecular complexes useful in the invention include those molecules carried by vectors. Typically, these vectors carry RNA or DNA molecules, although delivery of moieties other than nucleic acid molecules is encompassed by the present invention. The macromolecular complexes useful in the invention are not limited by size, but rather encompass molecules that, due to their large size, are not able to enter the cell on their own as well as molecules that can infect or transfect cells without the application of the present method. Examples of suitable vector constructs are provided in International Patent Application No. PCT/US2005/34283, which is incorporated by reference herein.

Methods for assembling and producing a variety of different constructs as defined herein are known to those of skill in the art and have been described in textbooks and in the literature. See, e.g., Sambrook et al, Molecular cloning: A Laboratory Manual, Cold Spring Harbor Press, Cold Spring Harbor, N.Y. (1989).

Construction of Cardiac Circuit

A circuit and surgical method useful in the method of the invention are described in detail as follows.

The basic structure of a human heart 10 is illustrated in FIG. 1. Oxygen-poor blood is returned to the right atrium 12 of the heart via two large veins, the superior vena cava 14 and the inferior vena cava 16, and is pumped into the right ventricle 18 and then to the pulmonary artery 20 before passing to the lungs. Oxygen-rich blood returns from the lungs via four pulmonary veins 22 into the left atrium 24, is pumped into the left ventricle 26, and thereafter, flows into the aorta 28 where it is circulated throughout the body. Coronary arteries (not shown) connect to the aorta 28 and provide oxygen-rich blood to the heart. A network of coronary veins (not shown) returns the oxygen-poor blood utilized by the heart into the right atrium 12 via the coronary sinus (not shown).

The heart can be isolated in situ via the formation of separate cardiopulmonary bypass circuits for cardiac and systemic circulation. As best illustrated in FIG. 2, right angle venous cannulae, 30 and 32, are positioned within the superior vena cava 14 and the inferior vena cava 16 and snares, 34 and 36, are placed about the superior vena cava 14 and the inferior vena cava 16 so that all systemic venous return flows into a systemic cardiopulmonary bypass circuit 38 via a Y-connector 40. The systemic circuit 38 can include a pump oxygenator 42, or like mechanism, and can return oxygen-rich blood to the subject's femoral and/or carotid arteries via a cannula (not shown). The aorta 28 and pulmonary artery 20 are cross-clamped with clamps 44 and 46 to further isolate cardiac circulation from systemic circulation.

In one embodiment, all four pulmonary veins 22 are isolated with snares 48 so that complete two-way isolation is accomplished in that cardiac circulation is isolated from systemic circulation and systemic circulation is isolated from cardiac circulation. The entire left atrium can alternatively be occluded using a single snare or clamp or balloon (not shown). This improves delivery of cells to the heart since cardiac circulation is prevented from being diluted with systemic circulation, providing a smaller circuit, and thus, permitting additional re-circulation through the circuit during cardio-pulmonary bypass (CPB).

Figure 3:
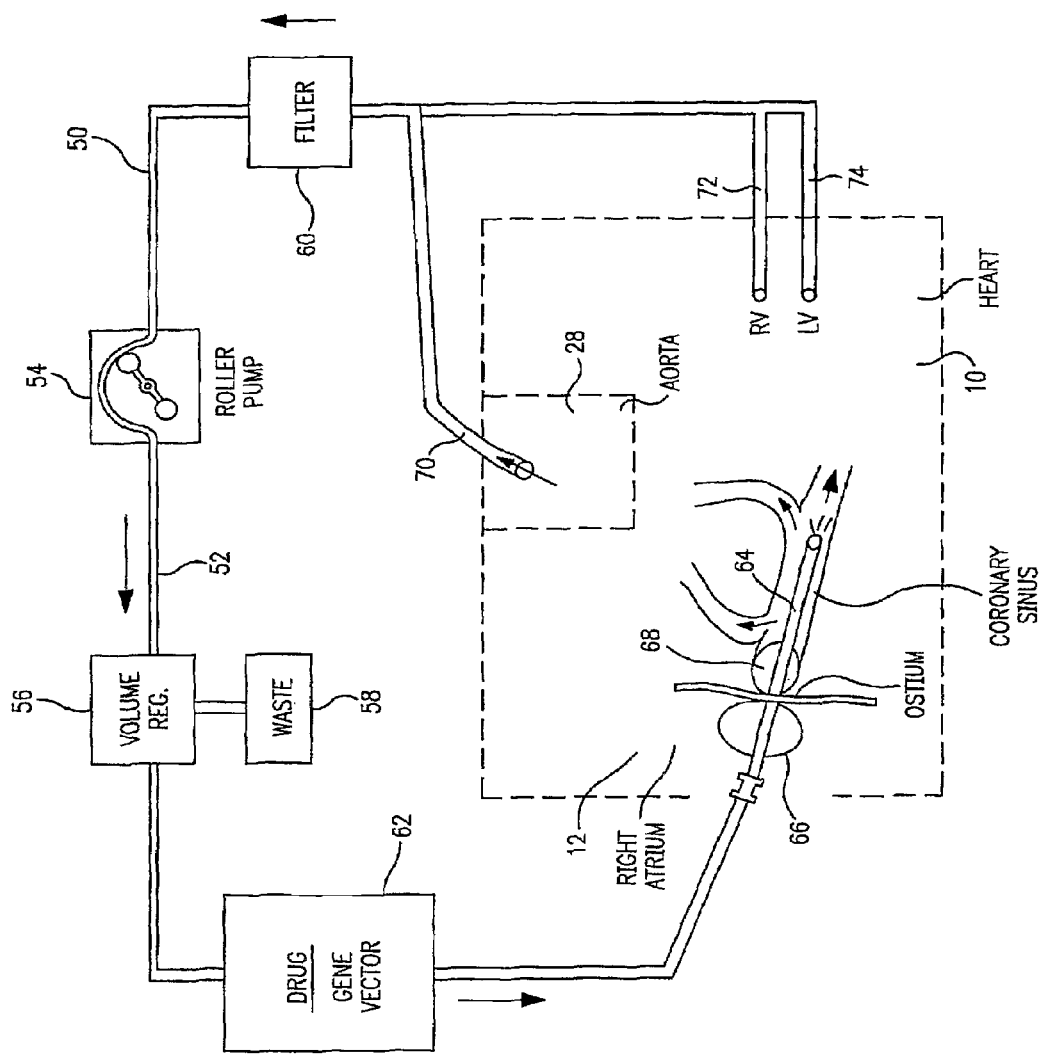
FIG. 3 is a schematic diagram of perfusion circuit useful in the present invention.
Figure 4:
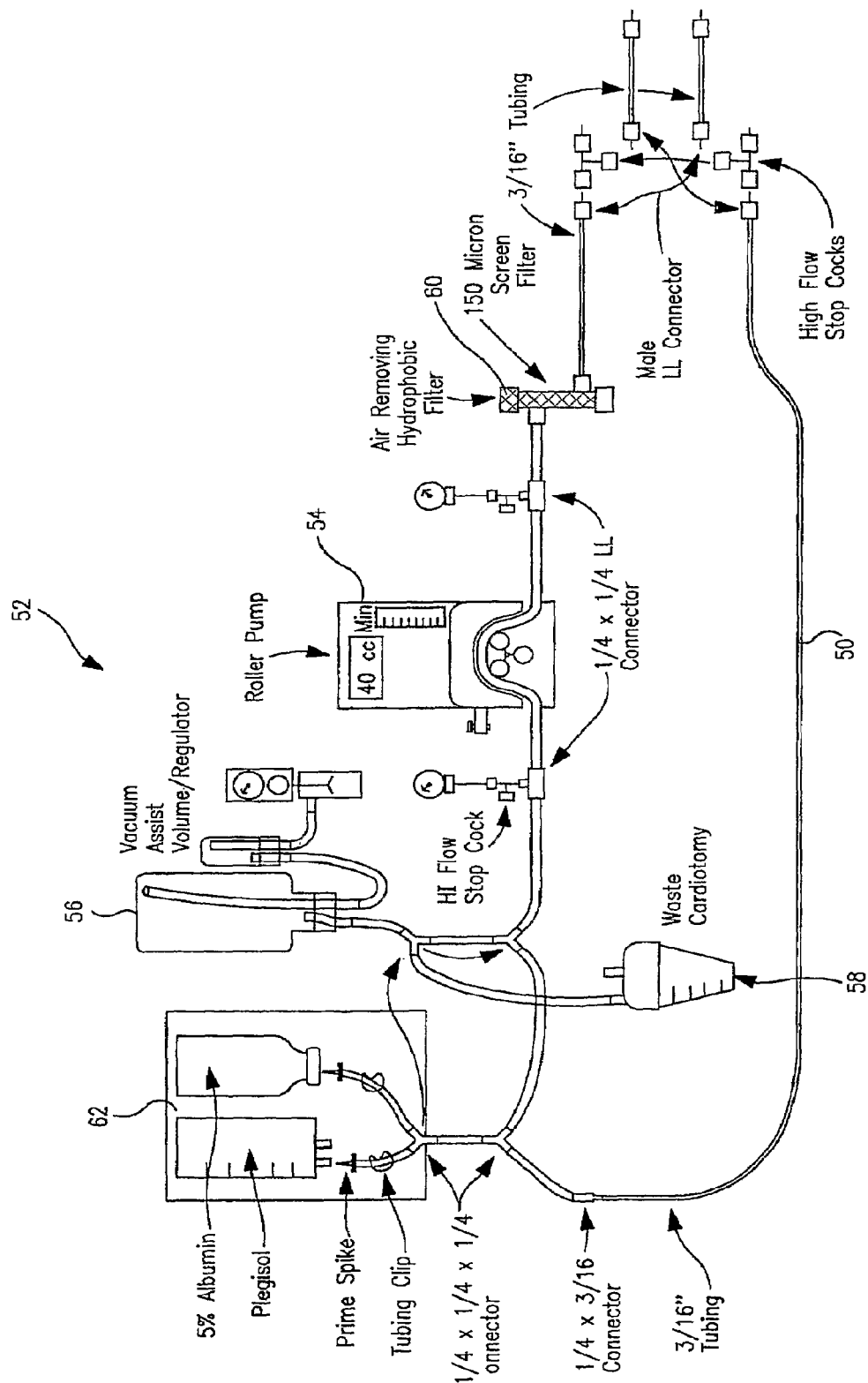
FIG. 4 is a view of an exterior part of the perfusion circuit.

As best illustrated in FIGS. 2 and 3, cardiac circulation follows a path defined by a perfusion circuit 50 which in one embodiment is retrograde. The path provides for retrograde perfusion via the coronary sinus, as illustrated in FIG. 3. Thus, the path permits multi-pass retrograde re-circulation of the cell-containing solution through the "completely" isolated coronary circulation within the heart. However, another embodiment provides a combination of retrograde and antegrade perfusion; this can be readily accomplished using the circuit of the invention. In yet another embodiment, antegrade perfusion is used.

As illustrated in FIGS. 2 and 3, the heart defines only a portion of the circuit 50. The exterior circuit part 52 includes a number of components that enhance the safety of the cardiac isolation procedure. Preferably, the exterior circuit part 52 includes a pump, such as a roller pump 54, for controlling the rate of circulation of the solution through the circuit 50. Preferably, a vacuum-assist volume regulator 56, or the like, is utilized to prevent distention of the heart due to volume gaining access to the cardiac circuit from the systemic circuit or elsewhere. Volume regulation is also important to ensure that priming volume is minimized to thereby maximize the concentration of the cells being recirculated through the retrograde coronary circulation path in the heart. A waste cardiotomy 58 can be utilized with regulator 56 to collect waste particulate debris from the circuit. Further, an air-removing hydrophobic filter 60 can be utilized to remove air bubbles from the circuit. In addition, the circuit part 52 includes apparatus 62 for the circulation of a selected drug or other moiety into the cardiac circulation.

In one embodiment, an albumin solution is delivered via this apparatus to the circuit components. This albumin solution, e.g., human serum albumin, can be used as a pre-treating prior to delivery of cells (or an optional macromolecular complex) to decrease the likelihood of killing the cells or decreasing the likelihood of cells binding to circuit components or inactivation of the complex during perfusion. Where desired, a variety of drugs can be delivered via the apparatus 62 including, e.g., Plegisol® cardioplegic solution, or other drugs, gene therapies and/or medication.

In addition, a vascular or endothelial permeability-enhancing agent can be delivered via this apparatus 62. Although the method of the invention is adapted for delivery of cells to the heart during total cardiac isolation, it may be desirable or necessary to utilize permeabilizing agents to facilitate delivery of the cells from the endothelium into the interstitium. Such agents include, e.g., histamine, acetylcholine, an adenosine nucleotide, arachidonic acid, bradykinin, cyanide, endothelin, endotoxin, interleukin-2, ionophore A23187, nitroprusside, a leukotriene, an oxygen radical, phospholipade, platelet activating factor, protamine, serotonin, tumor necrosis factor, vascular endothelial growth factor, a venom, and a vasoactive amine. See, e.g., WO 99/31982, Jul. 1, 1999.

Alternatively, if these agents are used, they may be co-infused with the cells as described below.

When utilized, the method of the invention may further include a rinse step following any dwell time. This rinse step can remove the permeabilizing agents from the circulation and avoid their exposure to the other organs which are outside the isolated circuit. Furthermore, the rinse step will remove cells that have not been engrafted into the myocardium, decreasing the potential for dissemination to other organs and tissues and limiting potentially harmful effects.

Finally, the exterior circuit part 52 can also include an oxygenator (not shown) and a heat exchanger (not shown) to allow control of the temperature and oxygen content of the solution being circulated through circuit 50.

The above described circuit 50 minimizes circuit volume, or priming volume, and protects the heart from the potentially deleterious effects of over-distention or perfusion of air into the cardiac circulation. In addition, the circuit enables a surgical technique to be utilized that provides high-efficiency, high-concentration delivery of cellular and/or genetic and other materials to the heart.

As stated above, cardiac circulation can be retrograde. In the context of cardiac surgery, retrograde refers to perfusion or infusion in the direction opposite of which blood ordinarily flow, i.e., from the veins to the arteries. Alternatively, cardiac circulation can be simultaneously retrograde, i.e., via the coronary sinus, and antegrade. Antegrade refers to when the flow goes in the direction normal for the cardiac.

According to one embodiment, a dumbbell-shaped balloon retrograde perfusion catheter 64 can form part of the circuit 50. The catheter 64 has a distal end including a pair of asymmetrical-shaped balloons, or balloon sections, 66 and 68, as described in U.S. Provisional Patent No. 60/504,743 filed on Sep. 19, 2003 and in its corresponding International Publication No. WO 2005/027995, published Mar. 31, 2005. The larger balloon, or balloon section, 66 is expanded within the right atrium to a size greater than the ostium and is advanced into engagement with the wall of the right atrium surrounding the ostium. The smaller balloon, or balloon section, 68 is located and expanded within the coronary sinus into engagement with the walls of the coronary sinus adjacent the ostium. Thus, an occlusive plug is formed at the ostium, and the balloons, or balloon sections, sandwich the ostium and anchor the catheter to the coronary sinus. Use of the catheter 64 enables global delivery of the circulating solution throughout the heart. For instance, improved delivery is provided to the right ventricle at maximal pressure gradient induction since venous "shunting" or "steal" of the solution back into the right atrium is prevented. The pressure gradient and elimination of shunting or steal facilitates and optimizes delivery of cells or other compounds globally throughout the heart. This embodiment disallows any cardiac venous effluent that enters the coronary sinus from escaping the retrograde infusion pressure and flow.

The circulating solution exits the heart via a cannula 70 placed within the aorta 28. Cannulae, 72 and 74, placed within the right and left ventricles 18 and 26, respectively, enable decompression of the right and left ventricles during circulation. Thus, the path of the circuit leads back to the exterior part 52 of the circuit 50 where bubbles, waste particulate debris, and excess volume are removed and where temperature and the concentration of drugs, gene vectors or the like is controlled.

Thus, circuit 50 permits safe and effective circulation and recirculation of cells (e.g., cardiac stem cells) through the heart and the surgical technique minimizes exposure of the stem cells to other organs within the subject's body.

In one embodiment, the present invention provides a method of treating myocardial infarction by forming a cardiac circuit that isolates a subject's cardiac circulation from the subject's systemic circulation; and perfusing a solution comprising cardiac stem cells into the cardiac circuit. In another embodiment, only partial isolation is achieved, while still allowing for recirculation of the cell solution through the heart multiple times even if there is progressive dilution of successive recirculations. In still another embodiment, the method of the invention permits a minimally invasive approach to be taken to achieve partial or complete isolation of the heart using balloon catheters to temporarily occlude some or all of the vessels: pulmonary artery, aorta, left atrium, pulmonary veins, inferior vena cava, superior vena cava. Optionally, cardiopulmonary bypass is not used in conjunction with complete or partial cardiac isolation.

Clinical Kit

In one aspect, the invention provides a kit for use by a clinician or other personnel. Typically, such a kit will contain a balloon catheter useful in the invention and, optionally, instructions for performing a method as described herein. A kit that is useful for performing the method of the invention is contemplated which comprises, in addition to the cells, balloon catheter and/or elements of the perfusion circuit, at least one disposable element of an extracorporeal circulatory support and oxygenation system. Preferably, such a kit comprises all of the single-use components needed to perform the method of the invention, including, an optional vascular permeability-enhancing agent, a fluid delivery instrument such as a syringe or a length of peristaltic pump tubing, and a cannula such as a hollow bore needle adapted to fit a syringe. Such a kit may also contain a pharmaceutically acceptable carrier, a second cannula, an oxygen-transporting agent, a clearance solution which is substantially free of the cells, one or more blood vessel occluding devices, such as a clamp, hemostat, or tourniquet, a disposable oxygenator, and the like.

All documents identified herein are incorporated by reference. While a preferred perfusion circuit and method have been described in detail, various modifications, alterations, and changes may be made without departing from the spirit and scope of the circuit and method according to the present invention as defined in the appended claims. The appended claims are intended to be construed to include all such embodiments and equivalent variations.

The invention claimed is:

1. A method of delivering a stem cell to a subject's heart, said method comprising the steps of:
   (a) forming a cardiac circuit that isolates a subject's cardiac circulation from the subject's systemic circulation; and
   (b) perfusing a solution comprising stem cells into the cardiac circuit in a retrograde direction.

2. The method according to claim 1, wherein the stem cells are selected from the group consisting of hematopoetic stem cells and cardiac stem cells, satellite cells, myoblasts and other multipotent precursor cells.

3. The method according to claim 2, wherein the cardiac stem cells are autologous cells expanded in culture from a biopsy taken from the subject.

4. The method according to claim 3, wherein the biopsy is taken from the subject's ventricle or atrium.

5. The method according to claim 1, wherein the stem cells are embryonic stem cells.

6. The method according to claim 1, wherein the cell solution is recirculated in the cardiac circuit for up to 30 minutes.

7. The method according to claim 1, wherein the subject's cardiac circulation is stopped to up to 10 minutes, thereby allowing the cell solution to dwell.

8. The method according to claim 7, wherein the subject's cardiac circulation is restarted and a second solution is infused in the circuit for up to 20 minutes.

9. The method according to claim 8, wherein the second solution is different from the first cellular solution.

10. A method of treating myocardiac infarction comprising the steps of:
    (a) forming a cardiac circuit that isolates a subject's cardiac circulation from the subject's systemic circulation; and
    (b) perfusing a solution comprising cardiac stem cells into the cardiac circuit in a retrograde direction.

* * * * *